United States Patent [19]

Koff

[11] 3,956,410

[45] May 11, 1976

[54] PURIFICATION OF CHLORONITROSOCYCLOHEXANE DIMER (CNCD)

[75] Inventor: Fred W. Koff, Long Valley, N.J.

[73] Assignee: Allied Chemical Corporation, New York, N.Y.

[22] Filed: May 28, 1975

[21] Appl. No.: 581,468

[52] U.S. Cl. ................................ 260/647; 260/707
[51] Int. Cl.² ......................................... C07C 81/02
[58] Field of Search .................................... 260/647

[56] References Cited
FOREIGN PATENTS OR APPLICATIONS
1,082,547   9/1967   United Kingdom................ 260/647

Primary Examiner—Leland A. Sebastian
Attorney, Agent, or Firm—Arthur J. Plantamura

[57] ABSTRACT

Purification of chloronitrosocyclohexane dimer (CNCD) is effected by dissolving the crude CNCD in a chlorinated aliphatic hydrocarbon or a lower aromatic hydrocarbon solvent and thereafter displacing the solvent of the solution with an aliphatic alcohol of higher boiling point. Pure CNCD crystallizes and is separated from the liquors, which retain colored matter and other impurities.

11 Claims, No Drawings

PURIFICATION OF CHLORONITROSOCYCLOHEXANE DIMER (CNCD)

BACKGROUND OF THE INVENTION

1. Field of the Invention

This invention relates to the purification of chloronitrosocyclohexane dimer (CNCD) which in its as produced relatively crude state must be freed of various impurities if it is to be useful in various applications, such as, for example, as an intermediate in the manufacture of L-lysine. The lysine process involves the subsequent steps of amination of the CNCD to aminocyclohexanone oxime (ACO); the Beckmann rearrangement of the ACO to produce α-amino-γ-caprolactam (ACL); the neutralization, isolation, resolution and racemization of the ACL to yield L-α-amino-γ-caprolactam hydrochloride (L-ACL.HCl) followed by hydrolysis of the L-ACL.HCl to yield L-lysine.HCl in high purity.

2. Description of the Prior Art

The reaction of nitrosyl chloride with olefins has been studied intensively and, for example, has played a major role in the structure determination and identification of terpenes. Depending on experimental conditions and olefin structures, the reaction leads to 2-chloro-1-nitrosoalkane dimers, chloro-oximes, chloronitro compounds, dichloro compounds, dichloronitroso compounds and nitro-nitroso compounds.

In particular, in the course of manufacture of L-lysine, 2-chloro-1-nitroso-cyclohexane dimer (CNCD) is derived from cyclohexane. The preparation of CNCD has long been known. U.S. Pat. No. 2,485,180, for example, describes the synthesis of CNCD and terpene derived dimers by using liquid SO₂ as the reaction solvent at preferred temperatures between −40° and −60°C. The chloro-nitroso dimer obtained from liquid SO₂ solvent appears to be the result of a trans addition of NOCl to the double bond and the structure has accordingly been assigned trans -2,2′-dichloro-trans-azodioxycyclohexene. The production of the dimer has in general been accompanied by substantial amounts of impurity which has interfered with or at least presented practical difficulties with the subsequent use of the intermediate to produce a product, i.e. lysine requiring high standards of purity.

SUMMARY OF THE INVENTION

In accordance with the procedures of the present invention, I have discovered a convenient and practical method for the purification of the chloronitrosocyclohexane dimer resulting in the production of CNCD of excellent quality and purity. This superior product has been achieved by dissolving the crude CNCD in a chlorinated aliphatic hydrocarbon solvent such as chloroform or a lower aromatic hydrocarbon solvent, such as benzene, which also dissolves undesirable color and other impurities and thereafter displacing said chlorinated solvent or aromatic solvent with a higher boiling aliphatic alcohol, e.g. ethanol. The solvent displacement causes CNCD to crystallize in a purified form, while colored matter and other impurities remain in solution. The purified CNCD can be separated from the impurity containing liquors by filtration or other conventional techniques. Upon subsequent reaction of the purified CNCD with ammonia, excellent yields of aminocyclohexanone oxime of high purity were obtained.

Thus, the invention provides a method which obviates the practical problems caused by impurities that are present in the chloronitrosocyclohexane dimer intermediate and that are present from the addition of NOCl to cyclo-olefins. The yields of aminocyclohexanone oxime by amination of the CNCD are correspondingly increased.

DESCRIPTION OF THE PREFERRED EMBODIMENTS

This invention is directed generally to the purification of the nitrosochlorination reaction product of a single cyclo-olefin or admixtures thereof, particularly to the nitrosochlorination product of cycloalkenes. The invention has particular application to the purification of CNCD resulting from the nitrosochlorination of cyclohexene. However, the invention may find useful application also with a variety of terpene-derived cyclo-olefins, e.g., cyclohexene, cycloheptene, cyclooctene, methyl cyclohexene, 8,9-dihydrolimonene, d- or l-limonene, dipentine, α- or β-pinene, or the like. The cyclo-olefin should preferably have one double bond, although cyclo-olefins with a multiplicity of double bonds such as cyclopentadiene may also be used as starting material in accordance with the invention.

The nitrosochlorination of cyclohexene to yield CNCD may be represented by the following reaction:

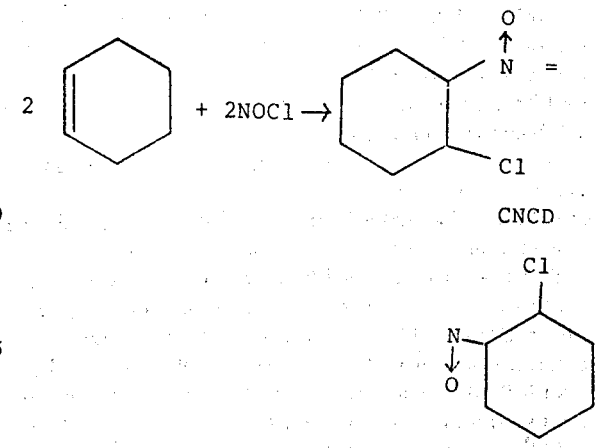

Cyclohexene and liquid SO₂ are fed to the nitrosochlorination reactor maintained at −10° to −30°C. while nitrosyl chloride is introduced with thorough stirring to prevent high local concentrations. A ratio of cyclohexene/nitrosyl chloride of about 1.05 to 1.10 is maintained in the feed stream.

While the quality of the cyclohexene (low peroxide concentration) and rigorous exclusion of air from the reactor and during work-up may improve yields and product quality to some extent, impurities at a level higher than normally tolerable in the subsequent reaction of CNCD with ammonia frequently are contained in the CNCD product.

The product is recovered from the reaction mixture in a variety of ways, e.g., by cooling the SO₂ solution and filtering the precipitated CNCD, or simply by evaporating the SO₂ solvent and washing the crude residue with another solvent, such as methanol. In either case, the CNCD obtained is not sufficiently pure for direct utilization in a synthesis of L-lysine.

While conventional recrystallization of CNCD from a variety of solvents is conceivable, such operation is not economical because of the relatively low solubility gradient of CNCD with temperature in most solvents.

I have found that purification of CNCD may be thoroughly and expeditiously effected by dissolving the crude CNCD in a chlorinated aliphatic hydrocarbon solvent such as chloroform or a lower aromatic hydrocarbon solvent, such as benzene, which readily dissolves CNCD and the accompanying impurities and then adding to the solution a higher boiling aliphatic alcohol and causing the chlorinated solvent or aromatic solvent to evaporate by application of heat and/or reduced pressure. During this operation CNCD crystallizes in a purified form, while colored matter and other impurities remain in solution. The purified CNCD may thereafter be separated from the impurity containing liquor by known techniques, such as filtration, centrifugation, etc. Due to the sensitivity of CNCD to prolonged heating the temperature during either the solubilization or the solvent displacement stage should not exceed approximately 100°C. and preferably should be below 80°C. While temperatures as low as 0°C. may be applied in either stage, these are not practical because of the necessity of using long contact periods in the dissolution stage and very low pressure in the solvent displacement stage. The preferred temperature range is from about 20°C. to about 60°C.

If the crude CNCD includes impurities which are not soluble in the chlorinated hydrocarbon or aromatic hydrocarbon solvent, said impurities can be eliminated by filtration or other conventional means prior to the solvent displacement stage.

In addition to chloroform, various other suitable chlorinated aliphatic hydrocarbon solvents, such as methylene dichloride, ethylene dichloride, 1,1,1-trichloroethane, carbon tetrachloride, 1-chloropropane, 1-chlorobutane, and the like may be employed. In addition to benzene, toluene may also be employed as a lower aromatic hydrocarbon solvent. Illustrative other displacing relatively higher boiling aliphatic alcohols in addition to ethyl alcohol, which may be employed, include methyl alcohol, n-propyl alcohol, isopropyl alcohol, n-butanol, sec-butanol, tert-butanol, and the like.

Although a particular chlorinated aliphatic hydrocarbon or lower aromatic hydrocarbon may have a higher boiling point than a particular aliphatic alcohol, a pair is chosen for purification of CNCD in such a manner that the aliphatic alcohol has a higher boiling point than the chlorinated solvent or the lower hydrocarbon. The difference in boiling point should be at least 5°C. and preferably more than 10°C. in order to effect an economic separation at the solvent displacement stage. For instance, if the aliphatic alcohol is methanol (b.p. 64.7°C.), the lower boiling solvent may be methylene dichloride (b.p. 40.2°C.); if the alcohol is ethanol (b.p. 78.4°C.), the lower boiling solvent may be methylene chloride or chloroform (b.p. 61.2°C.). Other suitable pairs will be obvious to those skilled in the art. A tabulation of the boiling points of some of the solvents applicable to this invention is presented below:

Boiling Point Chart

| Chlorinated or Aromatic Solvent | B.P. (°C.) | Aliphatic Alcohol | B.P. (°C.) |
|---|---|---|---|
| CH$_3$CHClCH$_3$ | 34.8 | Methanol | 64.7 |
| CH$_2$Cl$_2$ | 40.2 | Ethanol | 78.4 |
| CH$_3$CH$_2$CH$_2$Cl | 46.7 | iso-Propanol | 82.4 |
| CHCl$_3$ | 61.2 | tert-Butanol | 82.6 |
| CH$_3$CCl$_3$ | 74 | n-Propanol | 97.2 |
| CCl$_4$ | 76.8 | sec-Butanol | 99.5 |
| CH$_3$CH$_2$CH$_2$CH$_2$Cl | 78.5 | n-Butanol | 118 |
| Benzene | 80.1 | | |
| Toluene | 110.6 | | |

If desired, the chlorinated hydrocarbon solvents may be used in mixture with each other, or with aromatic hydrocarbon solvents, provided that the boiling point range of the mixture is lower than that of the aliphatic alcohol which is used in displacing these solvents. The aliphatic alcohols may also be used in mixture with each other, provided that the boiling point range of the mixture is higher than that of the solvent which is displaced.

The invention will be illustrated further by the following examples.

EXAMPLE 1

Crude CNCD, tan in color, 9.17 g, was dissolved in 30 ml chloroform at room temperature. A green-brown solution resulted containing also some suspended solids. The solution was filtered and 100 ml ethanol was added to the filtrate. The mixture was placed in a rotary evaporator and the volume was reduced to 35 ml at 40° to 50°C. under reduced pressure. The CNCD that crystallized was filtered, washed with ethanol and dried in vacuo at 60°C. Yield 8.08 g, or 88.1% of the charged material. The purified CNCD was white and of excellent chemical purity.

EXAMPLE 2

Crude CNCD, 114.2 g, was dissolved by stirring at 45°C. for 40 minutes with 350 ml chloroform. To the solution was added ethanol, 500 ml, and the mixture was flashed at 35°C. in a rotary evaporator under reduced pressure. When the volume had been reduced to 350 ml, the mixture was filtered, the crystals were washed with methanol and dried in vacuo at 60°C. The yield of purified CNCD was 99.1 g. An additional 3.9 g. CNCD was obtained by further reducing the volume of the filtrate to 50 ml.

EXAMPLE 3

Crude CNCD, 9.2 g, was dissolved at room temperature in 40 ml methylene chloride. The solution was placed in a rotary evaporator and solvent was distilled at room temperature while methanol was simultaneously added to the flask. When methylene chloride had been substantially replaced by methanol, the mixture (50 ml) was filtered, the crystals were washed with methanol and dried in vacuo at 50°C. The yield of purified CNCD was 8.0 g.

EXAMPLE 4

Crude CNCD, 8.16 g, was dissolved at room temperature in 40 ml benzene. The solution was placed in a rotary evaporator and the solvent was replaced by n-butanol as in Example 3. The mixture (50 ml) was filtered, the crystals were washed with n-butanol and dried in vacuo at 60°C. The yield of purified CNCD was 6.10 g.

EXAMPLE 5

Crude CNCD, 8.84 g, was dissolved in 40 ml chloroform at room temperature and the solvent was replaced by iso-propanol in similar manner as in Example 3. The mixture (50 ml) was filtered, the crystals were washed with iso-propanol and dried in vacuo at 50°C. The yield of purified CNCD was 7.51 g.

EXAMPLE 6 (COMPARATIVE EXAMPLE)

The following is an example of conventional crystallization from a single solvent: Crude CNCD, 5.00 g. was dissolved by stirring for 10 minutes with 500 ml methanol at reflux. The solution was concentrated to 100 ml in a rotary evaporator at about 30°C. Some crystals formed during concentration. The mixture was placed in a freezer at −30°C. for 16 hours and then filtered. The yield of purified CNCD was 3.48 g. An additional 0.39 g. of CNCD was obtained by concentration of the mother liquors to 20 ml and 15 hour cooling at −30°C.

While particular embodiments of the invention have been described hereinabove, it will, of course, be understood that this invention is not necessarily to be limited thereto, since various modifications may be made by those skilled in the art which are within the spirit and scope of the invention.

I claim:

1. A process for the purification of chloronitrosocyclohexane dimer (CNCD) comprising admixing said CNCD in a chlorinated aliphatic hydrocarbon or aromatic hydrocarbon selected from benzene or toluene or mixtures thereof until substantial dissolution of the CNCD has occurred, displacing said solvents with a higher boiling alkyl alcohol and separating the purified CNCD that crystallizes.

2. The process of claim 1 wherein the reaction mixture is filtered before displacement with said alkyl alcohol is effected.

3. The process of claim 1 wherein the chlorinated hydrocarbon is chloroform.

4. The process of claim 1 wherein the chlorinated aliphatic hydrocarbon is methylene chloride.

5. The process of claim 1 wherein the aromatic hydrocarbon is benzene.

6. The process of claim 1 wherein the aromatic hydrocarbon is toluene.

7. The process of claim 1 wherein the temperature is maintained at about 20°C. to 60°C.

8. The process of claim 3 wherein the displacing alcohol is selected from the group consisting of ethanol, iso-propanol and n-butanol.

9. The process of claim 4 wherein the displacing alcohol is methanol.

10. The process of claim 4 wherein the displacing alcohol is iso-propanol.

11. The process of claim 5 wherein the displacing alcohol is n-butanol.

* * * * *